US006826257B2

(12) United States Patent
Sayre et al.

(10) Patent No.: US 6,826,257 B2
(45) Date of Patent: Nov. 30, 2004

(54) DEVICE AND METHOD FOR MARGIN MARKING OF RADIOGRAPHY SPECIMENS

(75) Inventors: James Sayre, Farmington, CT (US); Stewart Bober, West Hartford, CT (US)

(73) Assignee: Beekley Corporation, Bristol, CT (US)

( * ) Notice: Subject to any disclaimer, the term of this patent is extended or adjusted under 35 U.S.C. 154(b) by 0 days.

(21) Appl. No.: 10/243,352

(22) Filed: Sep. 13, 2002

(65) Prior Publication Data

US 2004/0052333 A1 Mar. 18, 2004

(51) Int. Cl.⁷ .................................................. H05G 1/28
(52) U.S. Cl. ...................................... 378/163; 378/162
(58) Field of Search ............................... 378/162–164, 378/98.5, 37

(56) References Cited

U.S. PATENT DOCUMENTS 4,041,931 A   8/1977  Elliott et al. ................. 128/1 R
5,474,569 A   12/1995 Zinreich et al. .............. 606/151
5,640,438 A * 6/1997  Talluto et al. ................ 378/165
5,702,128 A   12/1997 Maxim et al. .................. 283/81
5,902,310 A   5/1999  Foerster et al. .............. 606/142

\* cited by examiner

*Primary Examiner*—Craig E. Church
*Assistant Examiner*—Jurie Yun
(74) *Attorney, Agent, or Firm*—McCarter & English, LLP

(57) ABSTRACT

A marking device for defining the margins and orientation of radiography specimens includes a plurality of visually distinctive markers joined by a base that holds the markers until the markers are secured to a specimen. The base serves as a holder for the individual markers as the markers are secured to a specimen with sutures or staples, at which time the markers are disconnected from the base. One or more markers may be secured to a specimen as needed to define the orientation of the specimen. By securing markers to specific locations on a specimen, a surgeon can indicate to radiologists and pathologists the specimen's orientation in the body before removal, thus aiding in future study of the specimen. Since the markers are made either wholly or partially from radiopaque material, the markers are visible when radiographed.

30 Claims, 6 Drawing Sheets

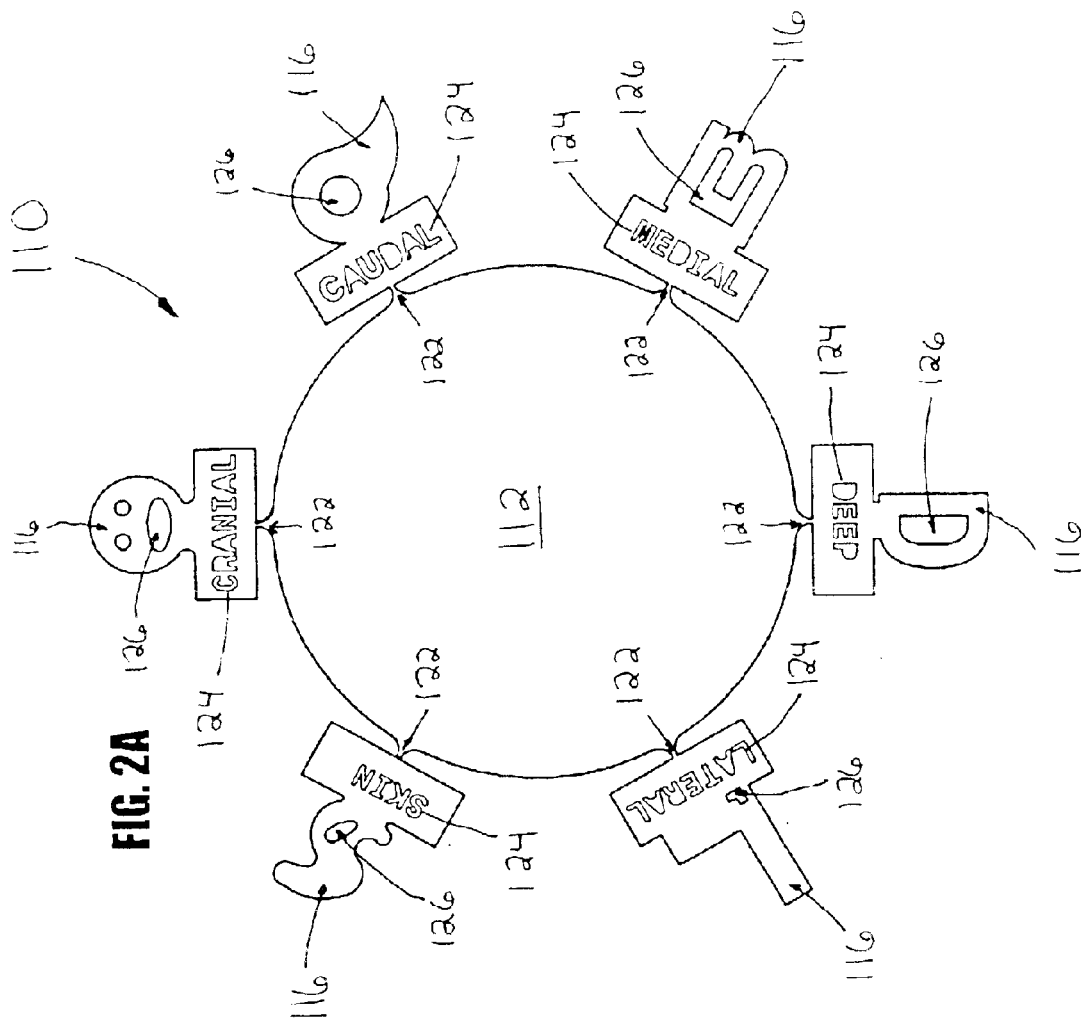

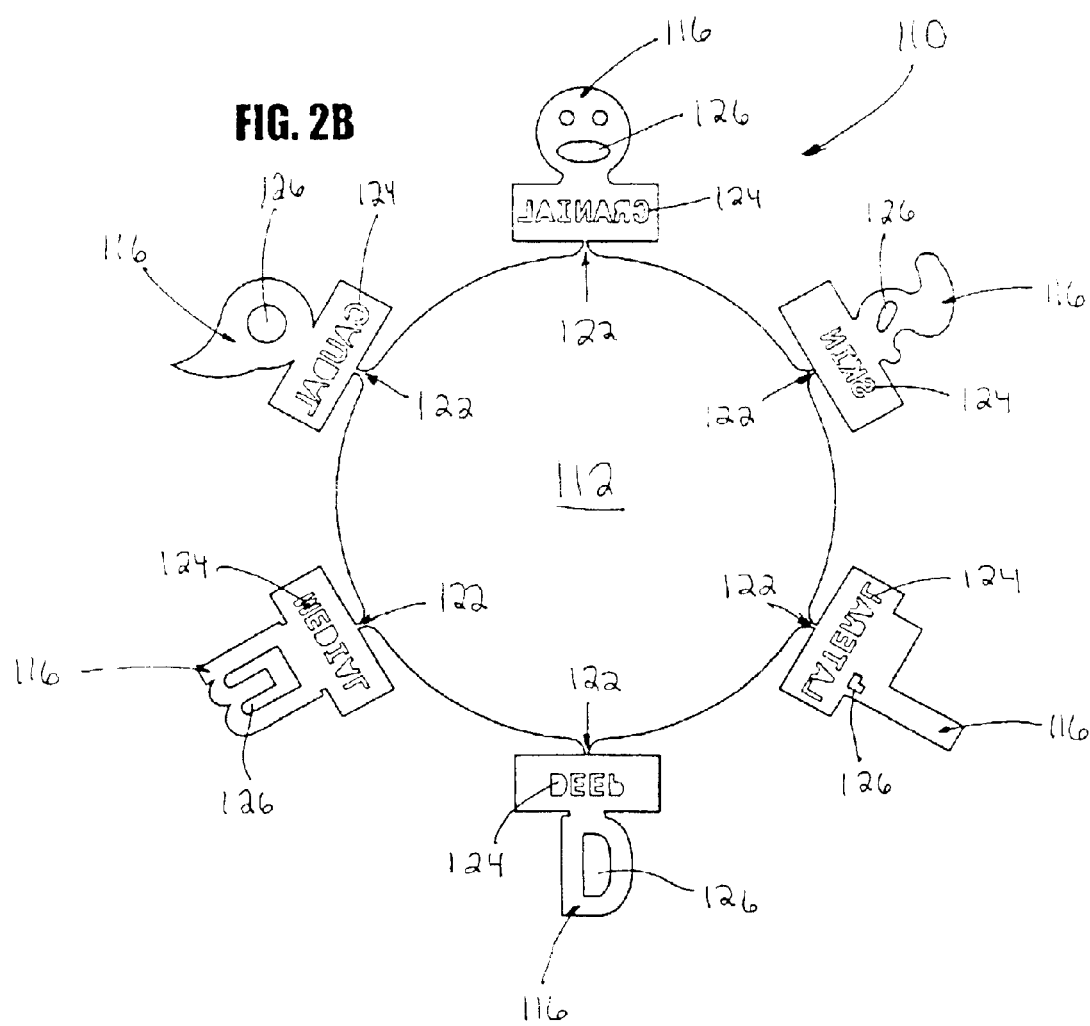

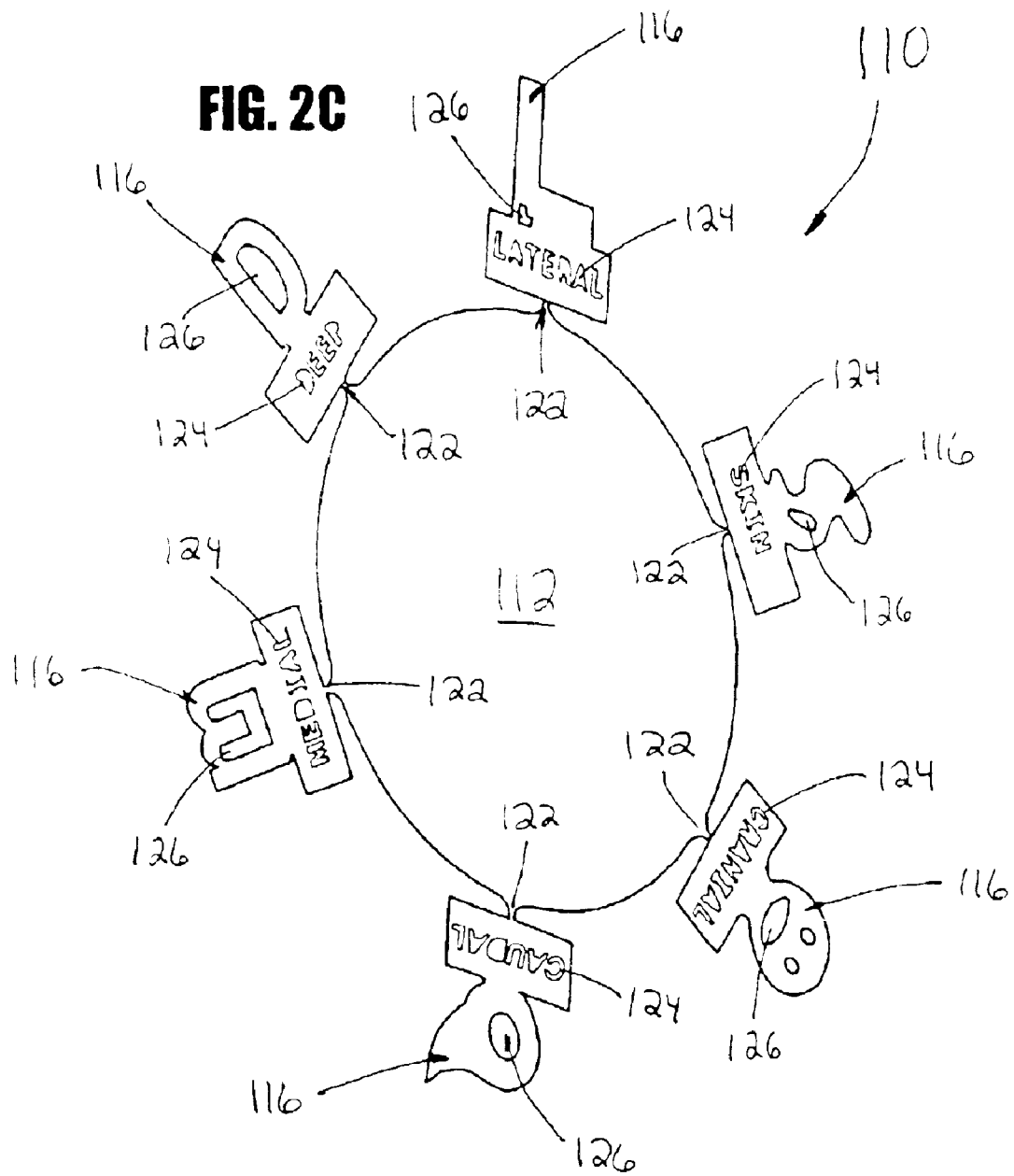

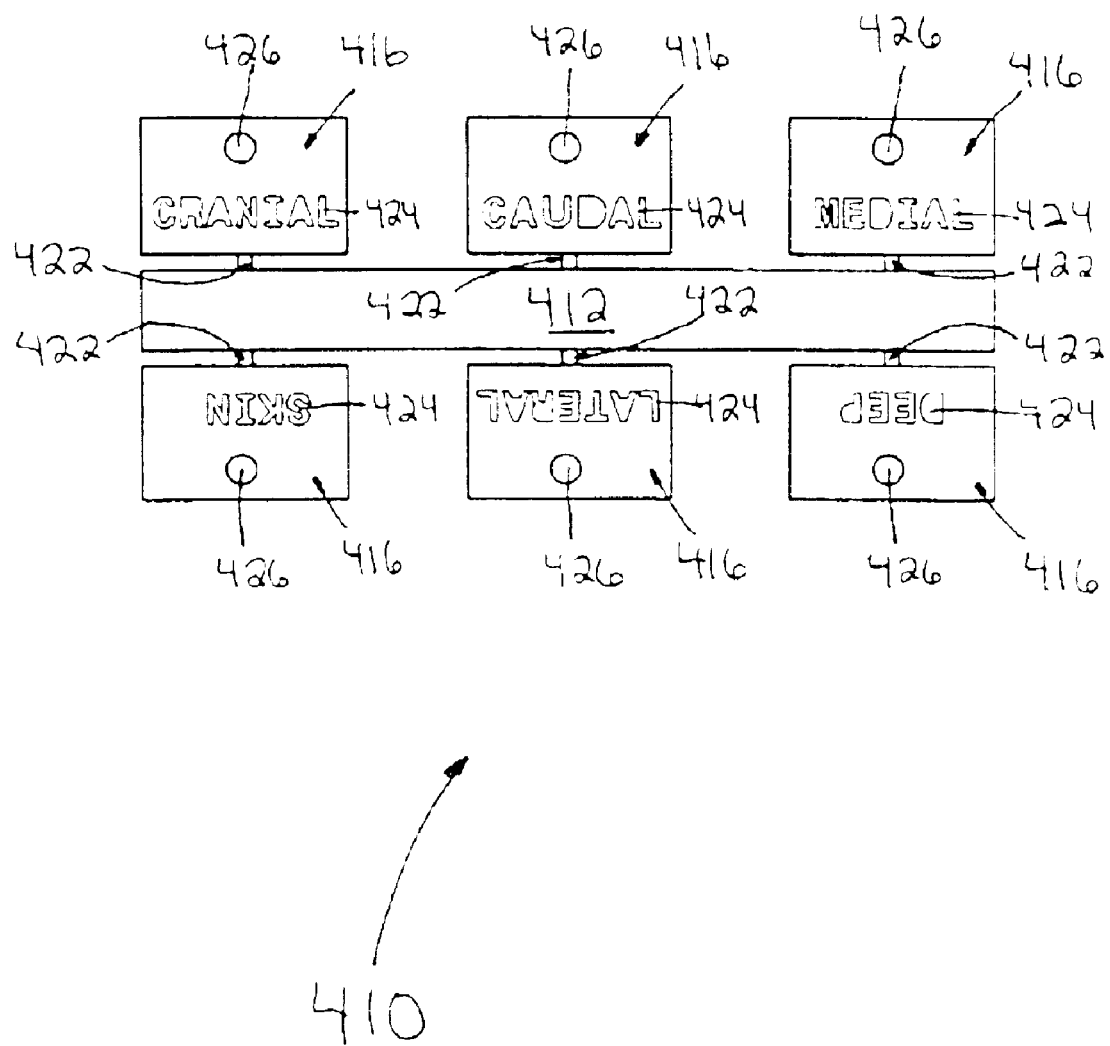

DEVICE AND METHOD FOR MARGIN MARKING OF RADIOGRAPHY SPECIMENS

FIELD OF THE INVENTION

The present invention relates to devices for marking radiography specimens, and in particular to devices that indicate the orientation of the specimen in a patient's body prior to removal. The present invention further relates to radiographic markers that will remain secured to specimens during manipulations accompanying radiography and pathology.

BACKGROUND INFORMATION

Radiologists frequently use markers that absorb xrays and cast an image when placed within an xray field to convey pertinent information on xray film. For example, right and left markers are routinely used to designate the anatomical orientation of the patient or to identify a particular extremity being examined. These types of markers are often placed on the surface of the examination table or xray film cassettes, within the exposure field but outside the image of the patient, to define the patient's physical orientation in relationship to the xray beam or the film.

Markers consisting of a radiopaque body and adhesive can be attached directly to the skin of patients. These markers give the radiologist a specific target for the xray and, since the radiopaque body will appear on radiographs later taken, help pinpoint the location of the area in question when reading the developed film. Some markers have been developed that can be inserted into the body to mark tissues or organs that require repeated xray monitoring. These types of markers are manufactured as staples or hooks (to attach to tissues), and even partial rings (to encircle grafted veins).

All of the previously described devices, while useful for specific purposes, have not been ideal for marking specimens removed from patients, as the described devices fail to address circumstances particular to specimen removal, radiography, and pathology. Successful removal of tumors from a patient's body requires an accurate evaluation of the excised tissue boundaries. To ensure that the entire tumor is removed, an adequate amount of healthy tissue surrounding the tumor is also extracted. The success of the surgery and the patient outcome is directly related to resection of the entirety of the tumor with an adequate healthy tissue boundary. For example, successful removal of breast tumors requires an accurate evaluation of the removed tissue boundaries to see if the tumor has effected the surrounding healthy tissue.

In the case of biopsies, a specimen is marked by the surgeon during removal from the patient. This mark aids the radiographers and pathologists in identifying the orientation of the specimen as it was present in the patient's body. Permanent marking of the exact orientation of the specimen is critical because of the manipulations—specimens must be pressed flat to properly xray—that take place during radiography. Presently, a surgeon may mark a tissue specimen by attaching sutures of various lengths, colors, or number combinations. The lengths, colors, or number of sutures convey to the pathologist the orientation of the gross pathology specimen in the patient's body. Unfortunately, this process of suturing and knotting may not be regularly performed because it is time consuming and requires detailed oral and/or written communications between surgeons, radiologists, and pathologists which can result in frustrations between the three professionals. Additional confusion may arise due to the fact that there is no standard marking method in the medical profession, since each surgeon develops his or her own method of marking.

Some radiopaque markers have been developed to address this problem, but still have some shortcomings. For example, existing markers can be attached to specimens by securing the markers with a clamping pair of pinchers, but these markers may release while the specimen is being radiographed and otherwise examined, and thus, the benefit is lost. Also, because such existing markers have sliding components and locking points, they tend to be thicker and larger than ideal. Since specimens must lay flat for proper radiography and pathology, a large, thick marker may obscure subtle pathology within the specimen. While the simple solution to this problem would be to decrease the marker size, if the marker is too small, it may be virtually impossible to hold while securing to a specimen. Existing devices also fail to standardize the method of marking specimens, thereby perpetuating the confusion and misinterpretation between the surgeon removing the specimen and the pathologist studying the specimen.

Accordingly, it is an object of the present invention to overcome the above-described drawbacks and disadvantages of existing markers.

SUMMARY OF THE INVENTION

The present invention is directed to a device for marking the margins of radiography specimens. The device includes a base and a plurality of markers detachably connected to the base. The base allows a user to easily grip the device while securing the small individual markers to a specimen. The base can take many forms from which the individual markers extend outwardly to facilitate attachment of the markers to specimens. The markers preferably include at least one aperture for receiving sutures, staples, or the like, which are used to secure the markers to specimens. After a marker is secured to a specimen, it can be broken away from the base of the device, thereby remaining secured to the specimen during radiography and pathology. The markers define distinctive, radiopaque marking indicia and/or shapes. The indicia (and/or the shapes of the markers themselves) are visible in a radiograph and indicate orientation of the specimen before the specimen was removed from the body.

One advantage of the present invention is that the device may standardize the marking system used to indicate the orientations of specimens, thereby eliminating confusion between the different medical professionals involved in treatment. Another advantage is that the device may remain fixedly secured to specimens during radiography because the device can be attached to a specimen with a suture, staple, or like connecting means, rather than relying on any pinching or squeezing elements that can accidentally release. Still another advantage is that the base of the device itself may be configured to be easily gripped during use, even though the markers themselves may be relatively small (so as to limit the amount of obstruction during x-ray). Yet another advantage is that the device may be able to retain multiple markers with various indicia, wherein one or more of the markers may be usable for the same or multiple specimens. Additionally, the device may be readily adaptable to mark all types of specimens and orientations.

These and other features and advantages of the invention are more fully disclosed or rendered apparent from the following detailed description of certain preferred embodiments of the invention, that are to be considered together with the accompanying drawings.

BRIEF DESCRIPTION OF THE DRAWINGS

FIG. 2 is a side view of the margin marking device;

FIG. 2A is a front view of the margin marking device;

FIG. 2B is a back view of the margin marking device;

FIG. 2C is a perspective view of the margin marking device;

FIG. 4 is a plan view of a third embodiment of a margin marking device of the present invention.

DETAILED DESCRIPTION OF THE PREFERRED EMBODIMENTS

Figure 1:
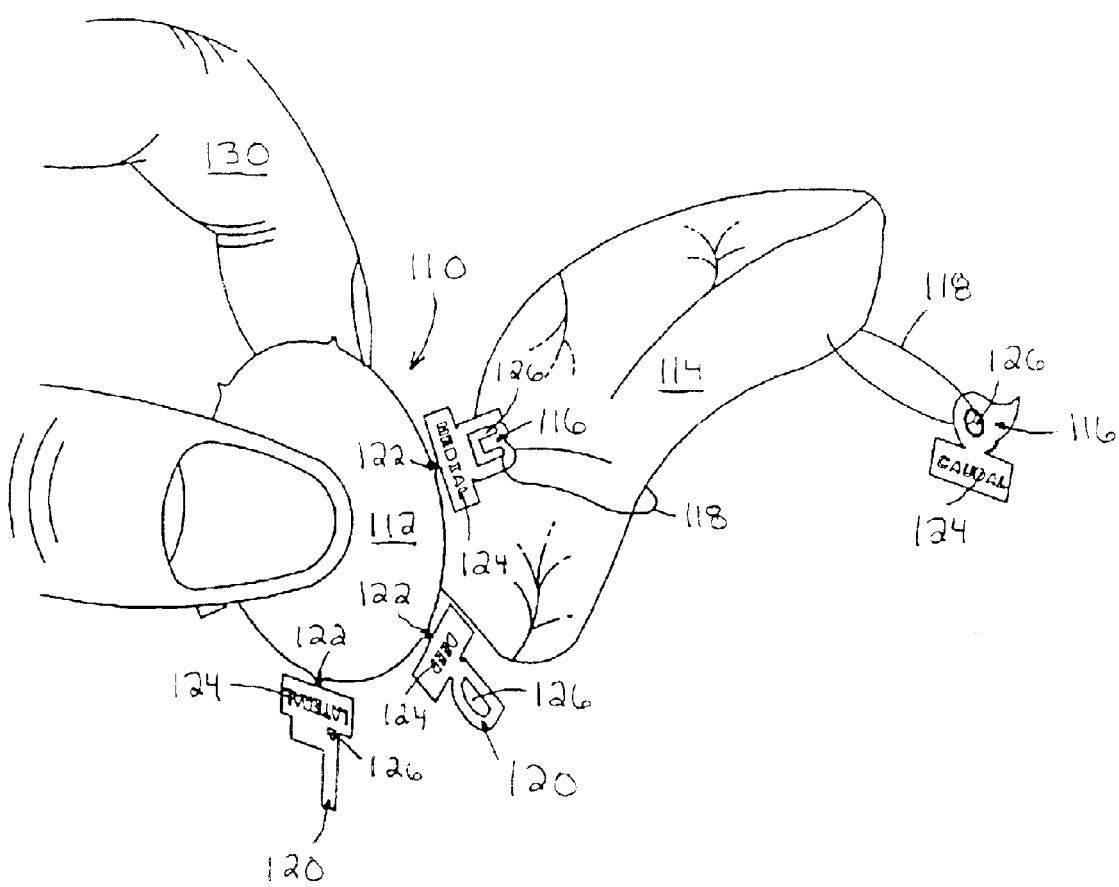
FIG. 1 is a rendering of a first embodiment of a device of the present invention for marking the margins of a specimen shown during use.

The present invention overcomes many of the problems that arise when other radiopaque markers are used to mark radiography specimens. The advantages, and other features of the disclosed device, will become more readily apparent to those having ordinary skill in the pertinent art from the following detailed description of certain preferred embodiments taken in conjunction with the drawings which set forth representative embodiments of the present invention and wherein like reference numerals identify similar structural elements.

In FIGS. 1, 2, and 2A–C, numeral 110 generally refers to a margin marking device. In FIG. 1, a marker 116 is being secured to a specimen 114 to mark the margins of the specimen. The marker 116 defines an aperture 126 sized to accommodate sutures 118, staples, or like connecting means for securing the marker 116 to the specimen 114. The sutures 118 may be any length, although longer lengths will allow the marker 116 to be moved away from the specimen 114 during radiography, thereby reducing or eliminating possible obstruction of the specimen 114 caused by the image of the radiopaque marker 116. A user 130 grips (with fingers, forceps, pliers, or other means) the base 112 while securing the marker 116 to the specimen 114. Once attached, the marker 116, because of its distinctive shape and indicia 124, identifies the orientation of the specimen 114 prior to removal from the patient's body. The user 130 then disconnects the marker 116 from the base 112 by breaking the marker 116 at a frangible connection 122. The user 130 may then mark different areas of the specimen 114 with the remaining markers 120 and/or may dispose of the device 110. Because the markers 116 are radiopaque, the markers 116 will appear on a radiograph of the specimen.

Referring now to FIGS. 2A–C, the base 112, frangible connections 122, and markers 116 are formed by photoetching a single piece of radiopaque material. For ease of handling the desirably small markers, each marker 116 is joined to the base 112 at a respective connection 122. The base 112 is of sufficient size to allow ease of handling the margin marking device 110, whether a user is using forceps, fingers, or other means to hold the base 112. The base 112 is circular, but those with ordinary skill in the pertinent art will notice that virtually any shape could be used for the base 112 including hexagons, triangles, rods, ovals, stars and other shapes. The connection 122 is strong enough to prevent inadvertent breakage, but weak enough to allow a user to disconnect the marker 116 from the base 112 once the marker 116 is attached to a specimen. The connection 122 can be a frangible connection (if the base and markers are constructed of a single piece of material, as shown), or can be any of numerous other types of connections that will allow for easy disconnection of the marker 116 from the base 112. Other such connections include, without limitation, wires, removable or breakable pins, hooks, adhesives, or the like.

As can be seen, each marker 116 defines a distinctive shape which, once attached to a specimen, indicates orientation of the specimen prior to removal. Indicia 124, also photoetched from the radiopaque material, aid in indicating orientation of each marker 116. In the illustrated embodiment, the indicia 124 are letters defined by apertures photoetched through the respective marker. Since the markers 116 are formed from radiopaque material, the markers will cast an image when radiographed, thus making the indicia 124 and/or distinctive shape of the marker 116 visible. As shown, the markers 116 each indicate orientation preferably by including indicia 124 in the form of one of the following words: "cranial," "caudal," "medial," "deep," "lateral," or "skin," and each marker further defines a peripheral shape forming a graphical representation of the respective indicia.

One of ordinary skill in the pertinent art will recognize that the indicia 124 can be formed through processes other than photoetching. For example, indicia 124 also may be formed in the radiopaque markers 116 by stamping, laser cutting, or by other means. In FIGS. 2A–C, the indicia 124 are defined by one or more apertures formed through the respective marker 116, those apertures defining the shapes of letters. Alternatively, the indicia can comprise distinctive shapes or other forms to provide unique identifying information. One of ordinary skill in the pertinent art also will recognize that the indicia themselves may be radiopaque. This method would allow the indicia to be mounted on or embedded in a non-radiopaque marker. In this case, indicia may be applied to each marker by printing the indicia thereon with a radiopaque ink or other suitable material. Radiopaque indicia could also be embedded within non-radiopaque markers while the markers are being formed (i.e., during casting, injection molding, or some other process).

It will be apparent to one of ordinary skill in the pertinent art that the markers 116, including the indicia 124 and/or the distinctive shapes of the markers, can define virtually any information relevant to the marking of specimens. Additionally, the marking system indicated, while directed to breast specimens, can be utilized with obvious modifications to mark any type of specimen, from any body part, for any purpose. A non-exhaustive list of possible alternative indicia include the words: "breast," "first," "second," "left," "right," "malignant," "base," "testicle," "anterior," etc. In addition, each marker may define a respective shape forming a graphical representation of the representative indicia or otherwise conveying desired information. Each marker 116 defines an aperture 126 large enough to accommodate sutures, staples or other attachment elements as desired, which allow fast attachment of the marker 116 to a specimen.

In the currently preferred embodiment of FIGS. 2A–C, the margin marking device 110 is approximately one inch in diameter, with each marker 116 defining a footprint of approximately 0.2 inches by 0.2 inches. The small size of the individual markers 116 allows for accurate marking of specimen margins and decreases the amount of specimen obstructed by the marker's image during xray. The base 112 and the markers 116 are both approximately 0.005 inch thick, which reduces the possibility of markers 116 impeding the required flattening of a specimen during radiography.

Those of ordinary skill in the pertinent art will note that the thickness and size of the markers 116 can vary depending on any of numerous different factors, such as the size of the specimen to which the markers 116 will be affixed (i.e., larger markers can be attached to larger specimens).

Those of ordinary skill in the pertinent art also will recognize that the margin marking device 110 can be made from any of numerous different materials that are currently or later become known for performing the function of the markers described herein. While FIG. 1 shows a marking device 110 made from a single piece of stainless steel, other radiopaque materials may be used, including platinum, titanium, lead, other metals or alloys, non-radiopaque materials with radiopaque coatings, or any combination of any of the foregoing. Additionally, non-radiopaque markers may be used with radiopaque indicia fixed thereon. In addition, the markers could be made of partially radiopaque, partially radiolucent material as disclosed in U.S. patent application Ser. No. 09/372,835, filed Aug. 12, 1999, entitled "An intermediate density marker and a method for using such a marker for radiographic examination", which is assigned to the assignee of the present invention and is hereby expressly incorporated by reference as a part of the present disclosure. This material would allow the image of the marker to appear on a radiograph yet would not obstruct any underlying structure of the specimen from being visible through the image of the marker on the radiograph.

Photoetching is the currently preferred method of making the margin marker system, since this process is relatively cost-effective, produces a precise reproduction of the original design, and produces a marking device that is burr and stress free. Photoetching also allows for a simple way to manufacture the entire device (base, connections, and markers) as a single piece. Other manufacturing processes such as stamping, casting, injection-molding, laser-cutting, and the like equally may be used.

Figure 3:
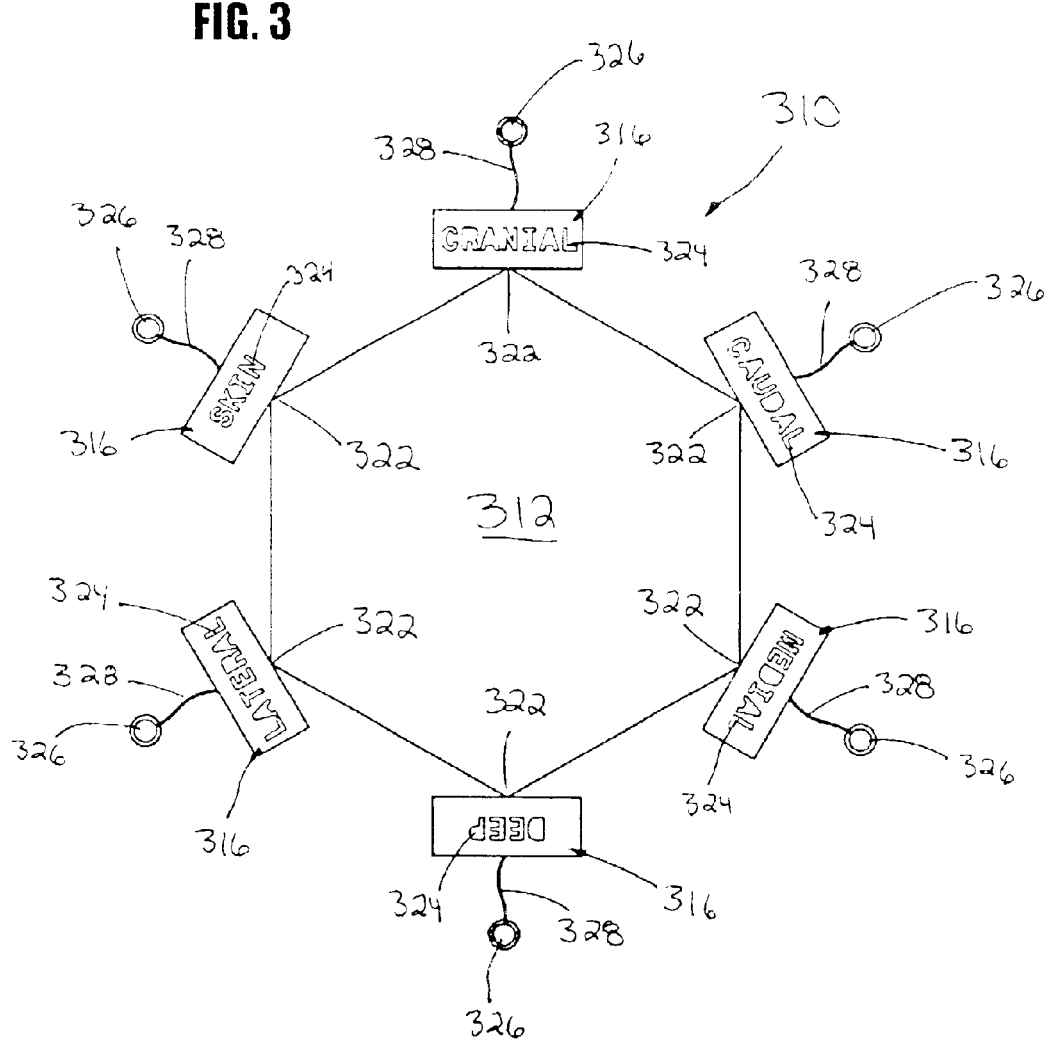
FIG. 3 is a plan view of a second embodiment of the margin marking device of the present invention.

Referring to FIG. 3, a margin marking device 310 defines a hexagonal base 312. As will be appreciated by those of ordinary skill in the pertinent art, margin marking device 310 utilizes the same principles of the margin marking device 110 of FIGS. 1 and 2A–C. Accordingly, like reference numerals preceded by the numeral "3," instead of the numeral "1," are used to indicate like elements. Each base 312 is connected to plate 316 at a respective connection 322. Each plate 316 is radiopaque and is photoetched with indicia 324 defining a respective unique orientation. Each plate 316 is connected to a respective wire 328 which is, in turn, connected to respective closed ring defining an aperture. The aperture 326 of each closed ring is sized to accommodate sutures, staples, or like connecting means, and may be fabricated from any of numerous materials available in the art and those developed in the future.

The length of each wire 328 may be set as desired. Alternatively, the wire 328 may be eliminated and each closed ring may be directly connected to the respective plate 316. The presence of the wire 328 is particularly useful for extremely small specimens, where little or no obstruction of the radiograph by the plate 316 would be acceptable. In this case, the closed ring can be fixed to a specimen, and the respective plate 316 can be moved away from the specimen during xray procedures, thereby eliminating possible obstruction of relevant portions of the specimen by the radiopaque plate 316. The wire 328 may be fabricated from radiopaque, non-radiopaque material, or partially radiopaque, partially radiolucent. A radiopaque wire 328 would be particularly useful, as it would be visible on a radiograph of the specimen, thereby defining a line from the respective plate 316 to the point of connection on the specimen. This would allow those viewing the radiograph to pinpoint the location of a particular point of interest on the specimen, without blocking that point with a radiopaque plate 316.

FIG. 4 shows a margin marking device 410 particularly well-suited to known methods of plastic construction. A rod-shaped base 412 is connected to markers 416 at frangible connections 422. Each marker 416 defines unique indicia, shown typically at 424, indicative of a respective orientation. The indicia 424 may be defined by one or more apertures formed through the respective marker 416, wherein the apertures define the shapes of letters and/or other unique identifying information. Alternatively, the indicia 424 may be applied to each marker 416 by printing the indicia thereon with a radiopaque ink or other suitable material. An aperture 426 is present in each marker 416 for attaching sutures, staples, or like attachment means. The margin marking device 410 can be molded as one piece of plastic or other suitable material. Each plastic marker 416 may be sufficiently radiopaque to mark the specimen. Alternatively, a radiopaque coating may be applied to each marker 416, or radiopaque material may be embedded or attached to the markers 416 in a manner known to those of ordinary skill in the pertinent art.

Although FIGS. 1 through 4 show margin marking devices having a plurality of markers connected to a base, one of ordinary skill in the pertinent art will recognize that the markers individually are novel in their own right. While the small size of the markers necessitates the use of a base to hold the markers as those markers are being fixed to specimens, this base is not necessary for larger markers, which can be stored in a container until they are secured to a specimen. These larger markers could be used to mark the margins of larger specimens, specimens where obstruction caused by the image of the marker during radiography is less of a concern, or for markers made of partially radiopaque, partially radiolucent material. The novelty of the present invention is not lost with an increase of marker size and the elimination of the base, as the advantages of a marker that remains secured to a specimen and standardizes the method of marking specimens still exist.

The skilled artisan also will recognize that any or all components of the margin marking device of the present disclosure (including the base and markers) could be made from many materials presently available in the art or invented in the future. If a marker is made from radiopaque material (or non-radiopaque material coated with radiopaque coating), indicia can be formed on the marker, either by photoetching, stamping or other means. The markers themselves also may define a distinctive shape without indicia, provided the markers are of such a shape as to clearly indicate a unique orientation or other requisite identifying information. Markers also may be completely non-radiopaque, with radiopaque indicia printed or otherwise fixed thereon. It also will be apparent to those of ordinary skill in the pertinent art that the base and markers may be manufactured from more than one piece of material or various combinations of materials. After manufacture, the markers could be attached to the base in any of numerous different ways that allow for disconnection during use. As indicated above, these points of connection between the markers and the base may be formed by hooks, wire, pins, frangible portions, or like connections.

Although the invention has been described in terms of exemplary embodiments, it is not limited thereto. Rather, the appended claims should be construed broadly, to include other variants and embodiments of the invention, which may be made by those skilled in the art without departing from the scope and range of the equivalents of the invention as defined by the appended claims.

What is claimed is:

1. A device for margin marking of radiography specimens, comprising:
   a base for gripping during use; and
   a plurality of markers detachably connected to said base, wherein each marker defines an aperture for attaching the marker to a specimen and indicia, and at least one of the marker and indicia is at least partially radiopaque and thereby visible when radiographed to indicate orientation of the specimen.

2. The margin marking device set forth in claim 1, wherein each marker is fabricated from radiopaque material.

3. The margin marking device set forth in claim 2, wherein a plurality of the markers each comprises a peripheral surface defining a unique shape.

4. The margin marking device set forth in claim 1, wherein each marker defines a unique orientation relative to the other markers.

5. The margin marking device set forth in claim 1, wherein each of the markers defines a unique orientation, including (i) a first marker defining a cranial orientation; (ii) a second marker defining a caudal orientation; (iii) a third marker defining a medial orientation; (iv) a fourth marker defining a deep orientation; (v) a fifth marker defining a lateral orientation; and (vi) a sixth marker defining a skin orientation.

6. The margin marking device set forth in claim 1, wherein each of the markers comprises indicia defined by at least one aperture.

7. The margin marking device set forth in claim 6, wherein each indicia includes characters indicative of a unique orientation.

8. The margin marking device set forth in claim 7, wherein each of the markers comprises a peripheral surface defining a unique shape and indicative of orientation.

9. A margin marker for radiography specimens comprising:
   a base and at least one marker detachably connected to the base, wherein the marker includes an aperture for attaching the marker to a specimen and indicia, and at least one of the marker and indicia is at least partially radiopaque and thereby visible when radiographed to indicate orientation of the specimen.

10. The margin marker set forth in claim 9, wherein the marker is fabricated from radiopaque material.

11. The margin marker set forth in claim 10, further comprising a peripheral surface defining a unique shape indicative of orientation.

12. The margin marker set forth in claim 9, wherein the marker is radiopaque and defines an orientation consisting of at least one of the following: cranial, caudal, medial, deep, lateral, and skin.

13. The margin marker set forth in claim 12, further comprising indicia defined by at least one aperture.

14. The margin marker set forth in claim 13, wherein each indicia includes characters indicative of a unique orientation.

15. A method of marking the margins of a radiography specimen comprising the steps of:
   providing a margin marking device having a base and at least one marker detachably connected to the base, and wherein the at least one marker defines an aperture and is at least partially radiopaque;
   gripping the base and holding the marker against or adjacent to a respective marginal portion of a specimen;
   securing the marker to the marginal portion of the specimen through the aperture and into the specimen; and
   disconnecting the marker from the base and leaving the marker secured to the marginal portion of the specimen to indicate the orientation of the specimen.

16. The method of marking set forth in claim 15, wherein the securing step is performed with at least one of a suture and a staple.

17. A method of marking the margins of a radiography specimen comprising the steps of:
   providing a device including a base and at least one marker detachably connected to the base and having indicia visible on a radiograph and indicative of orientation;
   securing the marker to a marginal portion of a specimen corresponding to the respective indicia disconnecting the marker and base;
   radiographing the specimen and marker attached thereto;
   displaying on the radiograph the indicia to thereby show the orientation of the specimen.

18. The method of marking set forth in claim 17, wherein the securing step is performed with at least one of a suture and a staple.

19. The method of marking set forth in claim 18, further comprising at least one of the following steps:
   (i) securing a marker with indicia indicative of caudal orientation to the caudal margin of the specimen;
   (ii) securing a marker with indicia indicative of medial orientation to the medial margin of the specimen;
   (iii) securing a marker with indicia indicative of deep orientation to the deep margin of the specimen;
   (iv) securing a marker with indicia indicative of lateral orientation to the lateral margin of the specimen;
   (v) securing a marker with indicia indicative of skin orientation to the skin margin of the specimen; and
   (vi) securing a marker with indicia indicative of cranial orientation to the cranial margin of the specimen.

20. A device for margin marking of radiography specimens, comprising:
   first means for marking a marginal portion of the specimen;
   second means for supporting the first means and for gripping during use;
   third means for visually indicating the orientation of the specimen on a radiograph;
   fourth means for detachably connecting the first means to the second means; and
   fifth means for securing the marker to the marginal portion of the specimen, wherein at least a portion of at least one of the first and third means is at least partially radiopaque.

21. The device for margin marking set forth in claim 20, wherein the first means is defined by a marker formed by a material that is at least partially radiopaque.

22. The device for margin marking set forth in claim 20, wherein the second means is defined by a base including at least one surface for gripping during use.

23. The device for margin marking set forth in claim 20, wherein the third means is defined by indicia.

24. The device for margin marking set forth in claim 23, wherein the indicia is defined by characters.

25. The device for margin marking set forth in claim 23, wherein the indicia is defined by a peripheral shape.

26. The device for margin marking set forth in claim 23, wherein the indicia is defined by at least one aperture.

27. The device for margin marking set forth in claim 20, wherein the fourth means is defined by a frangible portion.

28. The device for margin marking set forth in claim 20, wherein the fifth means is defined by at least one aperture for receiving at least one of a suture and a staple.

29. The device for margin marking set forth in claim 28, wherein the suture is sufficiently long to allow the first means to lie flat during a radiographic procedure.

30. The device for margin marking set forth in claim 20, wherein each of the first means and second means is approximately planar.

* * * * *